United States Patent [19]

Alemohammad

[11] Patent Number: 5,262,156

[45] Date of Patent: Nov. 16, 1993

[54] **ANTIGENIC COMPOSITIONS AND THEIR USE FOR THE DETECTION OF *HELICOBACTER PYLORI***

[75] Inventor: Mohammad M. Alemohammad, Mission Viejo, Calif.

[73] Assignee: Hycor Biomedical, Inc., Garden Grove, Calif.

[21] Appl. No.: 744,461

[22] Filed: Aug. 12, 1991

[51] Int. Cl.[5] .................. C07K 3/00; C07K 13/00; C07K 15/00; C07K 17/00
[52] U.S. Cl. ................... 424/92; 435/7.32; 435/7.92; 435/7.93; 435/7.94; 435/7.95; 436/513; 530/350
[58] Field of Search .............. 530/350; 435/7.32, 7.92, 435/7.93, 7.94, 7.95; 436/513; 424/92

[56] References Cited

U.S. PATENT DOCUMENTS 4,882,271  11/1989  Evans et al. .................. 435/12

FOREIGN PATENT DOCUMENTS 0329570  2/1989  European Pat. Off. .

OTHER PUBLICATIONS

Apel et al. (1988) Zbl. Bakt. Hyg. A 268:271–276.
Stacey et al. (1990) Eur. J. Clin Microbiol Infect Dis 9(10):732–737.
Drovet et al. (1991 Aug.) J. Clin. Microbiol 29(8):1620–1624.
Warren, J. R., Marshall, B. J., Unidentified curved bacilli on gastric epithelium in active chronic gastritis. *Lancet*, 1:1273–1275 (1983).
*Campylobacter pylori* becomes *Helicobacter pylori*. (editorial). *Lancet*, 2:1019–1020 (1989).
Blaser, M. J., Gastric Campylobacter-like organisms. *Gastroenterology* 93:371–383 (1987).
Rathbone, M. J. et al., *Campylobacter pyloridis*—a new factor in peptic ulcer disease? *Gut*, 27:635–641 (1986).
Hazell, S. L., Graham, D. Y., *Campylobacter pylori* in Perspective. *Practical Gastroenterology*, vol. XII, No. 7, pp. 11–15 (1988).
Dooley, C. P., Cohen, H., The Clinical Significance of *Campylobacter pylori*. *Annals of Internal Medicine*, 108:70–79 (1988).
Jones, D., *Campylobacter pyloridis* serology. *Serodiagn. Immunother. Infec. Dis.*, 1:87–89 (1987).
von Wuffen, H. et al., Immunoblot analysis of immune response to *Campylobacter pylori* and its clinical associations. *J. Clin. Pathol.*, 41:653–659 (1988).
Newell, D. G., Rathbone, B. J., Review Article: The serodiagnosis of *Campylobacter pyloir* infection. *Serodiagn. Immunother. Infec. Dis.*, 3:1–6 (1989).

*Primary Examiner*—Christine M. Nucker
*Assistant Examiner*—D. R. Preston
*Attorney, Agent, or Firm*—Lyon & Lyon

[57] ABSTRACT

The invention discloses antigenic compositions and an assay for detecting *Helicobacter pylori*. The antigenic composition includes a comprehensive mixture of fragments purified from *Helicobacter pylori* for the detection of Helicobacter pylori infection and/or for monitoring the status of such an infection following treatment. The assay involves an ELISA for urine samples, and includes a kit wherein the antigenic composition is immobilized on a solid support.

3 Claims, 2 Drawing Sheets

ANTIGENIC COMPOSITIONS AND THEIR USE FOR THE DETECTION OF *HELICOBACTER PYLORI*

FIELD OF THE INVENTION

This invention relates to antigenic compositions and their use for detecting the presence of antibodies specific to *Helicobacter pylori*. In particular, the invention relates to the clinical use of a novel mixture of antigens in a sensitive and specific assay for detecting the presence of *H. pylori* antibodies in a urine sample.

BACKGROUND OF THE INVENTION

*Helicobacter pylori* is a newly discovered bacterium found in the upper gastrointestinal tract of humans. Warren, J. R., Marshall, B. J. "Unidentified curved bacilli on gastric epithelium in active chronic gastritis." *Lancet*, 1:1273–1275 (1983). The bacterium was originally named *Campylobacter pylori* because it appeared to be a microaerophilic, spiral, gram-negative bacterium with the guanine and cytosine content normally found in the Campylobacter genus. However, it was later transferred to the Helicobacter genus when its ultrastructure and fatty acid composition were found to be very different from that of Campylobacters. "*Campylobacter pylori* becomes *Helicobacter pylori*." (editorial). *Lancet*, 2:1019–20 (1989). Its presence is associated with acute and chronic inflammation in the gastric antrum, gastritis and peptic ulcer disease. Blaser, M. J. "Gastric Campylobacter-like organisms." *Gastroenterology*, 93:371–383 (1987). In addition, the presence of *H. pylori* is an important marker for various inflammatory conditions of the upper gastrointestinal tract. Rathbone, B. J. et al. "*Campylobacter pyloridis*—a new factor in peptic ulcer disease?" *Gut*, 27:635–641 (1986). Detection of *H. pylori* can be achieved by many different techniques using either invasive or noninvasive methods. However, all of these current methods are flawed and/or inconvenient for the various reasons discussed below.

The current invasive methods require gastric biopsies and include culture, histology, and detection of preformed bacterial enzymes. Unfortunately, however, these methods are both time-consuming and uncomfortable for the patient. In addition, false-negative cultures are common—especially early on in the learning curve of laboratories. Hazell, S. L., Graham, D. Y. "*Campylobacter pylori* in Perspective." *Practical Gastroenterology*, Vol. XII, No. 7, pp. 11–15 (1988). In some instances, detection of the bacterium may be difficult because of a patchy distribution of *H. pylori* growth in the gastric mucosa. Moreover, failure to culture the organism may result from swallowed anesthetic, simethicone (as used during endoscopy), previous use of antibiotics, use of $H_2$-receptor antagonists, contamination of biopsy forceps with glutaraldehyde, biopsy of nongastric mucosa, and poor handling of or delay in plating specimens. Dooley, C. P., Cohen, H. "The Clinical Significance of *Campylobacter pylori*." *Annals of Internal Medicine*, 108:70–79 (1988). Many practitioners also work in clinics where culture procedures are not practicable, making alternative methods of detection more useful. Id. Hence, non-invasive methods were developed as an attempt to circumvent these problems, and to provide more useful alternative methods of detection.

Noninvasive procedures used to detect the presence of *H. pylori* fall into two groups: gastric urease detection by means of a breath test, and serology, where specific antibody detection systems are used to identify those individuals infected by the bacterium. Like the invasive procedures, however, the noninvasive procedures are also encumbered with problems.

*Helicobacter pylori* produces urease, an enzyme that hydrolyzes urea to form $CO_2$ and ammonia with a concomitant alkaline shift in pH. In the urea breath test, the patient is given $^{13}C$- or $^{14}C$- labelled urea with a beverage. The interaction of urease with the administered urea produces $CO_2$—which being membrane soluble, passes across the mucosa into the blood and into the breath where its concentration can be determined. Although this test can reliably detect an active *H. pylori* infection, it has many disadvantages including, inconvenience, cost in both materials and time, skilled personnel are required to perform the test, and the undesirable radiation exposure associated with the use of $^{14}C$-urea.

As a result, investigations with human serum were undertaken to replace the inconvenient and expensive procedures described above. The investigations revealed that *H. pylori* infections mediated a significant circulating antibody response against this organism; however, these antibody responses can be extremely inconsistent. Jones, D. "*Campylobacter pyloridis* serology." *Serodiagn. Immunother. Infec. Dis.*, 1:87:89 (1987).

Since the discovery of *H. pylori*, extensive studies have been performed on its antigens, and a wide variety of these antigens are now used for detection of *H. pylori* antibodies in serum. Immunoblotting studies have also demonstrated several major protein antigens that are detected by most sera. These include two urease-associated proteins (63 and 56 Kilodaltons (kDa)), a putative flagellin (54 kDa), and 116 and 48 kDa surface proteins and a 31 kDa outer membrane protein. von Wuffen, H. et al. "Immunoblot analysis of immune response to *Campylobacter pylori* and its clinical associations." *J. Clin. Pathol.*, 41: 653–659 (1988). In fact, U.S. Pat. No. 4,882,271 to Evans et al. describes a serum assay for the detection of *Campylobacter pylori* using the urease-associated antigens. Unfortunately, a number of these proteins share antigenic determinants with other Campylobacter species, most notably the putative flagellin, which results in a lack of specificity in the current serum assays. A particularly interesting protein of 116 kDa, however, appears to be *H. pylori* specific. Id. Table 1 summarizes the molecular weights of antigen fractions of *H. pylori* which have been reported.

TABLE 1

| *Helicobacter pylori* Antigens |
|---|
| Antigens (kDa) |
| 128 |
| 120 |
| 100–120 |
| 100–110 |
| 92 |
| 84 |
| 82 |
| 58–66 |
| 60 |
| 33 |
| 31 |
| 29 |
| 24 |
| 22 |
| 20 |
| 14–21 |

Current serological techniques to determine antibody responses against *H. pylori* include hemagglutination, bacterial agglutination, complement fixation and enzyme-linked immunosorbent assays (ELISA). ELISA appears to be the most sensitive, easiest and convenient of the test systems and is, therefore, the most commonly used. However, major problems have been encountered with the ELISA involving the source, type and characteristics of the antigen used. Newell, D. G., Rathbone, B. J. "Review Article: The serodiagnosis of *Campylobacter pylori* infection." *Serodiaon. Immunother. Infec. Dis.*, 3:1-6 (1989).

The literature reveals a tug-of-war between sensitivity and specificity, with adequate sensitivity producing inadequate specificity and vice versa. Studies using multiple antigens indicated that some sera from *H. pylori*-colonized patients could be negative against antigen from one strain but positive when tested against an antigen derived from several strains. Id. In addition, there is also an interspecies antigenic cross-reactivity. The putative flagellar protein of *H. pylori*, (molecular weight of about 60 kDa), which appears to be amongst the immunodominant antigens, has antigenic identity with the flagella of other Campylobacter species, especially the thermophilic group *C. jejuni* and *C. coli*. Id. Cross-reactivity appears to occur with the 31 kDa antigen as well. In addition to cross-reactivity, studies have demonstrated a strain variation among the *H. pylori* outer membrane antigens. As a result, until the present invention, a mixture of *H. pylori* antigens suitable for inclusion in an antigenic preparation for ELISA, that maintains both sensitivity and specificity, has been elusive.

EPO application No. 0329510 to Martin J. Blaser, purports to have discovered an antigenic composition which overcomes this tug-of-war. The antigenic composition described in that application comprises a mixture of fragments from five (5) strains of *H. pylori* which is enriched with at least one of the following antigens: 63, 57, 45 and 31 kDa fragments. However, the enriched presence of the cross-reactive 63 and 31 kDa fragments significantly impairs the specificity of this assay. Consequently, there is still a need for an antigenic composition which is at the same time, both highly specific and highly sensitive for antibodies directed against *H. pylori*.

In addition to the antigen-associated problems, the handling of blood and blood products poses significant biological hazards. Tests based on the detection of antibodies in serum involves blood collection and blood component separation procedures. While these procedures may not be complicated, they involve a degree of biological hazard, which includes needle sticks and contamination with blood-borne infectious agents. Because of this hazard, laboratory personnel prefer assays involving urine samples which provide greater hygienic protection against these risks.

With this in mind, it has been established that normal urine contains significant amounts of both IgG and IgA. There also appears to be a good correlation between levels of *H. pylori*-specific IgG in serum and in urine in infected individuals even though the immunoglobulin titer in urine is lower than in serum. Because the immunoglobulin titer is lower in urine than in serum, assays with low sensitivity may not be able to detect antibodies present in dilute urine samples. Hence, neither the Evans nor Blaser assays discussed above could produce reliable results in a urine sample.

In addition, urine can easily be obtained and procedures involving urine collection and testing are simple and essentially void of biological risk. Moreover, a urine assay provides laboratory personnel greater hygienic protection against the biological hazards associated with handling blood and blood-related products. Hence, there is a definite need for a highly specific and highly sensitive diagnostic test for detecting antibodies directed to *H. pylori* in a specimen which overcomes the problems discussed above. The present invention meets this need and provides related advantages as well.

Definitions

In the context of the present specification, antigen is used to refer to any substance that can elicit an immune response and that can react specifically with the corresponding antibodies or T cell receptors.

The term antibody means a substance that is produced in response to stimulation by an antigen and that reacts specifically with that antigen.

The term assay includes radioimmunoassay, ELISA, hemagglutination, bacterial agglutination, complement fixation, Western blot or other known detection methods.

Enzyme-linked immunosorbent assay or ELISA refers to a method for detecting the formation of antigen/antibody complexes.

The term fragment means any part of the *H. pylori* bacterium following disruption of the cell by any means, using any reagent or combination of reagents to produce bacterial antigens, and any derivatives thereof.

The term enriched refers to a concentration of one or more particular *H. pylori* antigens which exceeds their native concentration.

The term useful means that the antigens are present in infected individuals, absent in non-infected individuals, and do not cross-react with antibodies from other similar species.

The term test sample or sample or specimen includes any one or more selected from the group consisting of serum, plasma, lymphatic fluid, cerebral spinal fluid and urine.

SUMMARY OF THE INVENTION

It is a general object of the present invention to provide a highly specific and highly sensitive diagnostic assay for detecting an *Helicobacter pylori* infection.

It is another object of the invention to provide an antigenic mixture of *H. pylori* antigens which are specific for, and which bind with a high sensitivity to antibodies directed against *H. pylori*.

It is a further object of the invention to provide a simple and biologically risk free diagnostic assay for detecting antibodies directed against *H. pylori*.

It is yet another object of the invention to provide a highly specific and sensitive assay for antibodies directed against *H. pylori* in a dilute sample.

It is still a further object of the invention to provide an easy to use diagnostic kit for detecting an *H. pylori* infection.

It is another object of the invention to provide a clinical kit for detecting antibodies directed against *H. pylori* in a dilute sample.

It is a further object of the invention to provide a means to monitor the effectiveness of treatments against *H. pylori* infection.

These and other objects are readily achieved by providing a unique antigenic preparation made up of *H. pylori* fragments.

These fragments are both specific for *H. pylori* infection and are immunoreactive in patients with this infection. The antigenic preparation is composed of a mixture of different useful antigens of at least one strain of *H. pylori*, which react with antibodies present in *H. pylori* infected individuals, regardless of the infecting strains present, but which does not react with antibodies of non-infected individuals.

The comprehensive antigen preparation of the present invention includes a mixture of individual *H. pylori* proteins as identified by electrophoresis on sodium dodecyl sulfate polyacrylamide gel (hereinafter, "SDS-PAGE"). In addition, this mixture is enriched with at least one of the 116, 84, 19 and 14 kDa fragments. Antibodies to these particular antigen fragments appear to be present in all *H. pylori* infected individuals, and absent in non-infected individuals. Appropriate derivatives of the specified antigenic fragments, including synthetic and recombinant derivatives, may also be used.

The approximate molecular weights recited are calculated from calibration curves based on the relative electrophoretic migration pattern of known molecular weight standards: $\alpha_2$ macroglobulin (180 kDa); $\beta$-galactosidase (116 kDa); pyruvate kinase (58 kDa) and lactic dehydrogenase (36 kDa). These standards facilitate identification and approximation of the molecular weight for each particular fragment.

In accordance with the present invention, samples to be tested for *H. pylori*-specific antibody are contacted with the specific and sensitive antigenic compositions defined herein. This contacting is followed by determining whether the degree of antigen/antibody complex formation exceeds a threshold which indicates that the sample is positive for *H. pylori*-specific antibody. The formation of antigen/antibody complex is then detected by conventional techniques.

In one particular embodiment an enzyme-linked immunosorbent assay (ELISA) is used for detecting formation of antigen/antibody complexes. This assay includes the steps of immobilizing the complex antigenic mixture on a solid support, adding a sample to the immobilized antigenic preparation, contacting the sample and the immobilized antigenic preparation to form an antigen/antibody complex; adding an enzyme-conjugated anti-human IgG to the antigen/antibody complex, contacting the enzyme-conjugated anti-human IgG to the antigen/antibody, adding a substrate to conjugate to the enzyme, and quantitating the conversion of the substrate by the enzyme.

According to another embodiment of the invention, the test sample is urine.

According to still another embodiment of the invention, a kit is provided for carrying out the above-identified method. This kit includes, in one or more containers, the antigenic preparation of the invention combined with a solid support and a means for detecting the antigen/antibody complex. The kit can be administered in a hospital, clinic, or home setting for the diagnosis of an *H. pylori* infection or for monitoring the status of the infection following treatment.

These and other objects will become readily apparent to those skilled in the art from the following description and appended claims.

DETAILED DESCRIPTION

Figure 1:
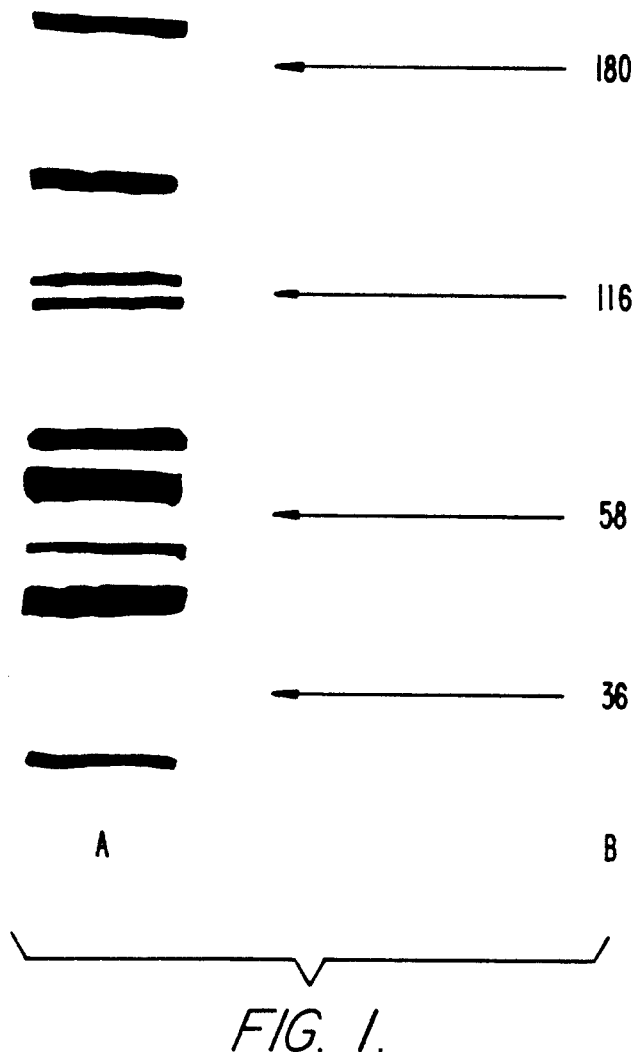
FIG. 1 is a Western Blot analysis of *H. pylori* antigens.

Two strains of *H. pylori*, obtained from the American Type Culture Collection (ATCC, Rockville, Md.), and bearing Accession Nos. 43504 and 43579, were used for preparation of the antigen composition. However, any two or more strains may be used for preparing the antigenic mixture. Urine and serum samples were obtained from individuals with known gastrointestinal disease; random samples were obtained as well. Seven samples were from patients with confirmed ongoing peptic ulcer diseases; four samples were from patients with confirmed gastritis undergoing treatment; and two samples were from patients with no known gastrointestinal illnesses. The urine samples were tested for the presence of IgG antibodies to H. pylori; the serum samples were tested for the presence of both IgG and IgA antibodies to *H. pylori*.

Bacteria and Growth Conditions

The bacteria obtained from the ATCC were grown on blood agar plates containing Vancomycin, Polymyxin B and Trimethoprim. Specific ingredients are listed below.

| INGREDIENTS | FINAL pH 7.4 |
| --- | --- |
| Proteose Peptone | 15.0 g |
| Liver Digest | 2.5 g |
| Yeast Extract | 5.0 g |
| Sodium Chloride | 5.0 g |
| Agar | 12.0 g |
| Vancomycin | 10.0 mg |
| Polymyxin | 2500.0 I.U. |
| Trimethoprim | 5.0 mg |
| Horse Blood (laked) | 70.0 ml |
| Distilled Water | 1000.0 ml |

One skilled in the art will recognize that different media comprised of different ingredients may be used for the same purpose. Culture plates were incubated at 37 C for four (4) days in a microaerophilic environment with high humidity using conventional techniques. Cells were then harvested in saline using a sterile metal spreader. The saline (containing the harvested cells) was centrifuged at 3000 rpm for twenty (20) minutes, and the saline solution thereafter retained. This technique for harvesting cells causes release of most of the antigen fractions into the retained saline solution.

Preparation of Antigens

The harvested cells (2.5 gm wet weight) were resuspended in 100 ml of a 1% solution of octyl-beta-D-glycopyranoside in phosphate buffer at pH 7.2. The cells were shaken at medium speed for two (2) hours at room temperature. The cell preparation was subsequently centrifuged at 13000 xg for fifteen (15) minutes. The supernatant was dialyzed at 2°-8° C. against 200 volumes of phosphate buffered saline (PBS) with three (3) changes.

Thereafter, the detergent-free cell extract was mixed with saline containing the *H. pylori* antigen fractions released during harvesting and this mixture was tested by Western Blot, using confirmed positive patient serum.

SDS-PAGE and Western Blot

Figure 2:
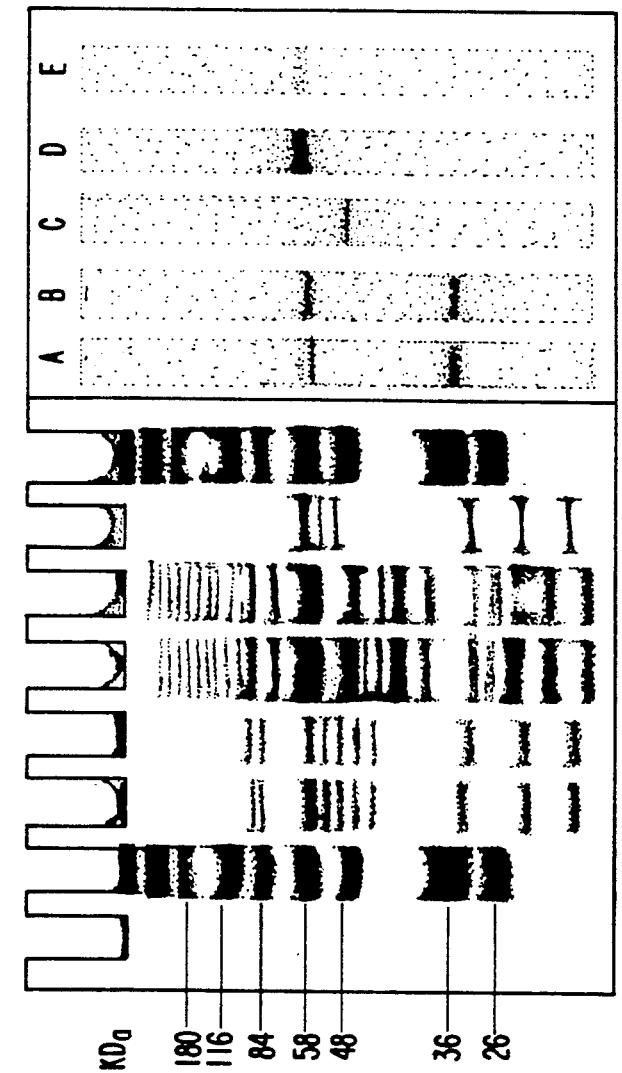
FIG. 2 is an SDS-PAGE and Western Blot analysis of *H. pylori* antigens.

The protein components of the antigen preparation were separated on a pre-prepared SDS-PAGE (Bio-Rad, Richmond, Calif.). The separated proteins were then electrophoretically transferred to nitrocellulose paper. The paper was blocked, washed, and incubated with diluted serum and concentrated anti-*H. pylori* in urine. The paper was incubated again with anti-human IgG alkaline phosphatase conjugate (Jackson Immuno Research, West Grove, Pa.) and subsequently stained with Naphthyl Phosphate Fast Red system. FIG. 1 identifies by Western Blot the *H. pylori* fragments present in the antigenic mixture. The molecular weight markers are indicated on the right hand side and are as follows: $\alpha_2$ macroglobulin (180 kDa), $\beta$-galactosidase (116 kDa), pyruvate kinase (58 kDa) and lactic dehydrogenase (36 kDa). FIG. 2 confirms the antigen profile presented in FIG. 1 by an SDS-PAGE analysis and Western Blot. On the SDS-PAGE, lanes 1 and 7 contain molecular weight markers, lanes 2 and 3 contain *H. pylori* antigens, lanes 4 and 5 contain *C. jejuni* antigens, and lane 6 contains reused *H. pylori* antigens. In the Western Blot, lanes B and E contain *H. pylori* antigens, lanes C and D contain *C. jejuni* antigens, and lane A contains reused *H. pylori* antigens. As illustrated in FIGS. 1 and 2, the antigenic preparation obtained by these methods contains almost all the known *H. pylori* antigen fractions. Moreover, FIG. 2 demonstrates the specificity of the antigenic preparation, wherein only one band, at 58 kDa, reacted weakly with *C. jejuni* positive serum. The purified antigenic preparation was then used in affinity chromatography for collecting urine and serum antibodies and for coating microtiter wells in an ELISA system.

Affinity Chromatography

The purified antigenic preparation, in PBS at pH 7.2, was attached to washed Affi-Gel 10 (Bio-Rad, Richmond, Calif.). The coated gel was then poured into a column and unbound materials were washed away using PBS, pH 7.2. To block the non-specific binding sites, the gel was incubated with IM hydroxylamine, pH 8.2. A positive serum sample or a large volume of diluted urine was recycled through the column at 4. C for 24 hours and unbound materials were washed with PBS, pH 7.2. Bound antibodies were then eluted with glycine buffer, pH 2.2, and the eluted antibodies were collected in a fraction collector. Purified concentrated immunoglobulins in urine were analyzed in a Western Blot. Specific antibodies against *H. pylori* in serum prepared by affinity chromatography were used as a control sample to compare with the urine antibodies.

ELISA

One skilled in the art will readily recognize that numerous methods can be used to detect *H. pylori* antibody in sera or urine. However, the preferred embodiment for the present invention involves the ELISA method and a urine sample.

Polystyrene microtiter wells were coated with 100 µl of the purified *H. pylori* antigenic preparation. After blocking the non-specific binding sites with 2% Bovine Serum Albumin (BSA), 100 µl of diluted serum or undiluted urine was added and incubated for twenty (20) minutes at room temperature. Goat anti-human IgG (or anti-human IgA) peroxidase conjugate (Jackson Immuno Research, West Grove, Pa.) was added to each well. After twenty (20) minutes incubation at room temperature, 70 µl of the substrate solution was added. The reaction was stopped after three (3) minutes by the addition of 70 µl of IM $H_3PO_4$. Color development was measured at 450 nm using a microtiter plate reader. The average absorbance at 450 nm for each sample was compared with that from a clinically confirmed patient, used as a positive control. Each sample was assayed in duplicate.

Table 2 presents the data obtained by ELISA using both patient sera and urine. Specific IgG and IgA in serum and specific IgG in urine against *H. pylori* was determined in thirteen (13) confirmed and thirty-one (31) random samples. Samples 1-6 were from patients examined for ulcer diseases by conventional methods, including endoscopy. Samples 7-10 were from patients who were positive but had been treated for eradication of ulcers; these samples were taken after treatment. Sample 11 had been confirmed positive, but serum was not available. Samples 12 and 13 were negative and served as control in this study. Samples 14-44 were random samples. Of the random samples, sample 14 was positive for both IgG and IgA (3.3% of random samples).

As observed and tabulated in Table 2, in all samples clinically confirmed for ulcer, the IgG titer in serum and urine, and the IgA titer in serum tested positive when the microtiter wells were coated with the antigenic preparation of the present invention. Four (4) patients which were positive for ulcer but undergoing treatment gave a low positive test. Healthy control samples were all negative. These results confirm the superior sensitivity of this method.

TABLE 2

| Patients | ELISA TEST RESULTS | | |
|---|---|---|---|
| | | Serum | Urine |
| Sample | Confirmed | IgG | IgA | IgG |
| 1 | Yes | + | + | + |
| 2 | Yes | + | + | + |
| 3 | Yes | + | + | + |
| 4 | Yes | + | + | + |
| 5 | Yes | + | + | + |
| 6 | Yes | + | +/− | +/− |
| 7 | Yes | +/− | − | ND* |
| 8 | Yes | +/− | +/− | +/− |
| 9 | Yes | +/− | − | − |
| 10 | Yes | +/− | − | − |
| 11 | Yes | ND* | ND* | + |
| 12 | Yes | − | − | − |
| 13 | Yes | − | − | − |
| 14 | No | + | + | ND* |
| 15 | No | +/− | − | ND* |
| 16-44 | No | − | − | ND* |

*ND = Not Determined

KIT

An *H. pylori* specific test kit for detecting antibodies can be prepared in several ways. One such test kit for antibody detection can be comprised of a compartmental enclosure containing a plurality of wells with plates comprised of any charged membrane or plastic material. These plates may be coated prior to use with the *H. pylori* antigenic preparation of the present invention. The plates may also be coated prior to use with ELISA materials for enzyme detection, consisting of peroxidase labelled goat anti-human IgG or the like, and a color change indicator. However, these same reagents may also be supplied in one or more separate containers. The kit may also include controls for false positives and false negatives and can be used for one sample or multiple samples.

It is to be emphasized that the terms and descriptions used herein are preferred embodiments set forth by way of illustration only, and are not intended as limitations on the many variations which those of skill in the art will recognize to be possible in practicing the invention. Modifications and other uses will occur to those skilled in the art which are encompassed within the spirit of the invention or defined by the scope of the following claims.

I claim:

1. An antigenic preparation for detecting antibodies specific to *Helicobacter pylori*, said preparation consisting essentially of a mixture of fragments from at least one strain of *Helicobacter pylori* and having an enriched concentration of fragments having a molecular weight of 116 kilodaltons, 84 kilodaltons, 19 kilodaltons and 14 kilodaltons.

2. An antigenic preparation according to claim 1 wherein said preparation reacts with antibodies present in *Helicobacter pylori* infected individuals, but does not react with antibodies of non-infected individuals.

3. The antigenic preparation according to claim 1 wherein said preparation is able to detect antibodies specific to *Helicobacter pylori* in a urine sample.

* * * * *